(12) United States Patent
Kunert

(10) Patent No.: US 6,305,842 B1
(45) Date of Patent: Oct. 23, 2001

(54) X-RAY EXAMINATION APPARATUS INCLUDING A DIAPHRAGM UNIT

(75) Inventor: Heinz-Peter Kunert, Tangstedt (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/376,858

(22) Filed: Aug. 18, 1999

(30) Foreign Application Priority Data

Aug. 19, 1998 (DE) .............................................. 198 37 512

(51) Int. Cl.⁷ ...................................................... G21K 1/02
(52) U.S. Cl. .......................... 378/206; 378/147; 378/150; 378/205
(58) Field of Search .................................. 378/205, 206, 378/150, 147

(56) References Cited

U.S. PATENT DOCUMENTS

| 3,921,001 | * | 11/1975 | Edholm et al. | 378/206 |
| 4,670,896 | * | 6/1987 | Klausz | 378/156 |
| 5,136,627 | * | 8/1992 | Conrads et al. | 378/206 |
| 5,563,924 | * | 10/1996 | Winkelmann | 378/150 |
| 5,684,854 | * | 11/1997 | Hughes | 378/206 |
| 5,844,962 | | 12/1998 | Kunert | 378/150 |
| 6,036,362 | * | 3/2000 | Schmitt | 378/206 |
| 6,219,403 | * | 4/2001 | Nishihara | 378/65 |
| 6,229,873 | * | 5/2001 | Bani-Hashemi et al. | 378/63 |

FOREIGN PATENT DOCUMENTS 07148159   6/1995   (JP) .

* cited by examiner

Primary Examiner—David V. Bruce
Assistant Examiner—Allen C Ho
(74) Attorney, Agent, or Firm—John E. Vodopia

(57) ABSTRACT

The invention relates to an X-ray examination apparatus which includes an X-ray source and a diaphragm unit which is connected to the X-ray source and is provided with shutters for limiting a radiation cone beam emanating from the focal spot of the X-ray source, and also includes a light source for generating a light cone beam which traverses the shutters via a mirror. When the dimensions of the light-emitting parts of the light source are significantly larger than the focal spot, the irradiation field irradiated by the radiation cone beam is smaller than the illuminated field illuminated by the light cone beam. In order to match the irradiation field with the illuminated field, the shutters are provided with correction shutters which are transparent to X-rays but impervious to light and limit the light cone beam.

2 Claims, 2 Drawing Sheets

X-RAY EXAMINATION APPARATUS INCLUDING A DIAPHRAGM UNIT

BACKGROUND OF THE INVENTION

1. Field of the Invention

The invention relates to an X-ray examination apparatus which includes an X-ray source and a diaphragm unit which is connected to the X-ray source and is provided with shutters for limiting a radiation cone beam emanating from a focal spot of the X-ray source, and also includes a light source for generating a light cone beam which traverses the shutters via a reflector device. The invention also relates to a diaphragm device for an X-ray source.

2. Description of the Related Art

An X-ray examination apparatus and a diaphragm unit of the kind set forth are known from U.S. Pat. No. 5,844,962.

Therein, the light cone serves as an aid which facilitates the adjustment by the user of the irradiated field exposed to the X-rays during a subsequent X-ray exposure. The light cone then illuminates either the patient to be examined or, in the case of an X-ray examination apparatus provided with a grid drawer, the grid drawer when the X-ray source and the grid drawer with the film to be exposed are temporarily pulled to a position to the side of the table top on which the patient is accommodated. The illuminated surface should then correspond to the surface exposed to the cone beam of the X-ray source during a subsequent X-ray exposure.

The light source is then situated at the same optical distance from the shutter plates as the focal spot of the radiation source. The light source should be as inexpensive as possible, have a long service life and a high brightness, and the light cone defined thereby should correspond as accurately as possible to the radiation cone formed during a subsequent X-ray exposure. The dimensions of light sources, i.e. the structure emitting the light, for example the filament of the light source, however, are large in comparison with those of the focal spot of the X-ray source. Consequently, the surface illuminated by the light source is larger than the surface subsequently exposed to the X-rays.

In order to match the surface irradiated by the X-ray source and the surface irradiated by the light source, the known X-ray examination apparatus is provided with a motor drive for the shutters, which drive is controlled in such a manner that during the adjustment by means of the light source the diaphragm aperture is smaller than during a subsequent X-ray exposure. This solution necessitates the presence of an appropriately controlled motor drive.

SUMMARY OF THE INVENTION

It is an object of the present invention to provide an X-ray examination apparatus as well as a diaphragm unit which do not require a motor drive so as to achieve matched illuminated and irradiated fields. This object is achieved according to the invention in that the shutters are provided with correction shutters which are transparent to X-rays but impervious to light and limit the light cone. A correspondingly constructed diaphragm unit is a further object of the present invention.

Because they are transparent to X-rays the correction shutters according to the invention do not affect the radiation cone but limit the light cone. When the correction shutters are suitably proportioned, the illuminated field and the irradiated field can thus be matched. Exact matching of this kind can be achieved only for a defined distance between the focal spot and the image converter (for example, a film). For other distances (Bucky exposure apparatus usually operates with a defined distance, for example 1.15 m) such matching is no longer exact, but is significantly better than in the absence of correction shutters.

Simple X-ray examination apparatus may have one or more different diaphragm apertures, each one of which limits the radiation cone. In that case the correction shutters should constrict the diaphragm apertures on all sides. Contemporary X-ray examination apparatus, however, comprise two preferably adjustable pairs of diaphragm plates for limiting the radiation cone in two mutually perpendicular directions. An embodiment of the invention which is suitable for such X-ray examination apparatus is such that the shutters include two preferably adjustable pairs of shutter plates having pair-wise parallel shutter edges for limiting the radiation cone beam in two mutually perpendicular directions, and that a correction shutter is connected to each shutter plate in such a manner that its edge extends parallel to the shutter edge. The correction shutters can then be arranged in different manners.

In another embodiment, the correction shutters connected to a pair of shutter plates are situated in the same plane. The correction shutters are then situated at the same side for each pair of diaphragm plates. However, in that case the correction shutters obstruct the complete closing of the pair of diaphragm plates. Such complete closing, however, usually is not necessary.

In a further embodiment which enables complete closing of the pairs of diaphragm plates, the correction shutter are situated in different planes. In an additional embodiment, the focal spot of the X-ray source is inclined relative to the planes of the correction shutters, and the offset between the planes of the correction shutters is chosen to be such that the asymmetry of the radiation cone beam, imposed by the inclination, is at least partly compensated for by a corresponding asymmetry of the light cone beam. The non-symmetry occurring for one of the two pairs of diaphragm plates in an X-ray tube having a strip focus can thus be removed.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
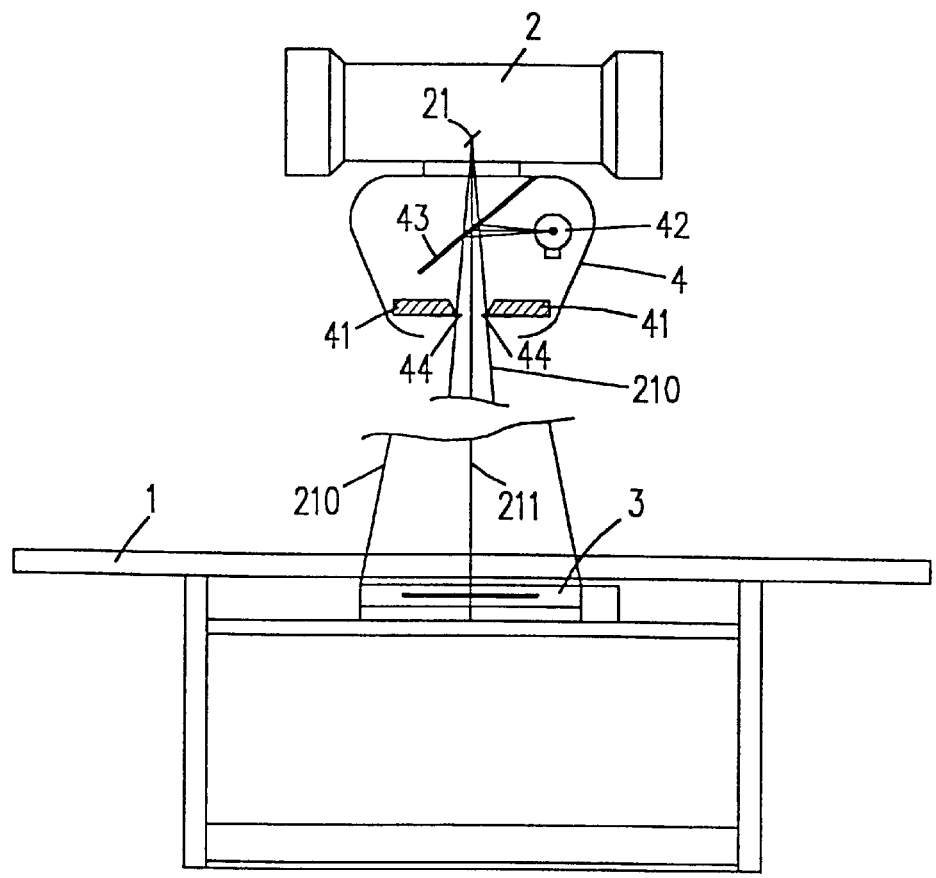
FIG. 1 shows a Bucky X-ray examination apparatus according to the invention.

FIG. 1 shows a Bucky X-ray examination apparatus which includes a patient table 1 and an X-ray source 2. Underneath the top of the patient table 1 there is arranged a moving grid 3 which is displaceable in the longitudinal direction of the table top and is provided with a film to be exposed during an X-ray exposure. The X-ray source 2 is supported by a stand (not shown) which is displaceable in the longitudinal direction of the table, the source being displaceable from a position in which its radiation cone is incident at the center of the table top, perpendicularly to the plane of drawing, to a position in which it is situated perpendicularly above the moving grid 3 pulled underneath the table top. The desired exposure format can be adjusted in this position.

Beam limiting is performed by means of a diaphragm unit 4 which is mounted on the X-ray source 2. The X-rays, emanating from the focal spot or the focus 21 of an X-ray tube which is included in the X-ray source 2 but not shown, are limited by a first pair of shutter plates 41 having shutter edges which extend parallel to one another and perpendicularly to the plane of drawing of FIG. 1. There is also provided a second pair of shutter plates (not shown) which has horizontal shutter edges which extend parallel to the plane of drawing and limit the X-rays in the direction perpendicular to the plane of drawing. The radiation cone limited by the shutter plates is denoted by the reference 210; the radiation cone is interrupted by the wavy lines because in practice the distance of the X-ray source 2 is larger than shown in FIG. 1. The ray at the center of the radiation cone, the so-called central ray, is denoted by the reference 211. It is incident at right angles at the center of the moving grid 3.

The diaphragm unit 4 includes a light source 42 which illuminates the table top (or a patient accommodated thereon) via a mirror 43, being transparent to X-rays, and through the diaphragm plates 41. The light source 42 is situated at the same distance from the mirror 43 as the focal spot 21. Therefore, if it (or the light-emitting structure included therein) were to have the same dimensions as the focal spot 21, the light cone limited by the shutter plates 41 should correspond to the radiation cone 210 and hence the illuminated field (i.e. the cross-section of the light cone in the plane of the film contained in the moving grid 3) should correspond to the irradiated field (the cross-section of the radiation cone 210 in the plane of the film present in the moving grid 3).

For the reasons stated above the light-emitting structure of the light source (for example, the filament of an incandescent lamp) is significantly larger than the focal spot. In practice the dimensions of the filament may be, for example 6×3.2 mm whereas the (optically effective) dimensions of the focal spot are 1×1 mm or less. In the case of such a large filament, the umbra (that is the region which is not exposed to any light) is substantially larger than the region exposed to light from all light-emitting points of the light source. The edge of the illuminated field is then situated (comparatively readily reproducible) at approximately 8% of the brightness at the center. Consequently, the illuminated field that can be observed by the user is also significantly larger than the fully illuminated field which corresponds essentially to the irradiated field.

The image defect defined by the difference between these fields amounts to approximately 15 mm in the direction of the greater filament width for the given dimensions of the filament and a distance of 1 m between the film and the focus 21, and to approximately 35 mm in the case of a distance of 2 m. In order to reduce or eliminate such image defects, the shutter plates 41 are provided with correction shutters 44 whose edges extend parallel to the edges of the shutter plates 41 and constrict the light cone. Because the correction shutters, however, are made of a material which is transparent to X-rays, the radiation cone 210 is not influenced thereby.

Figure 2:
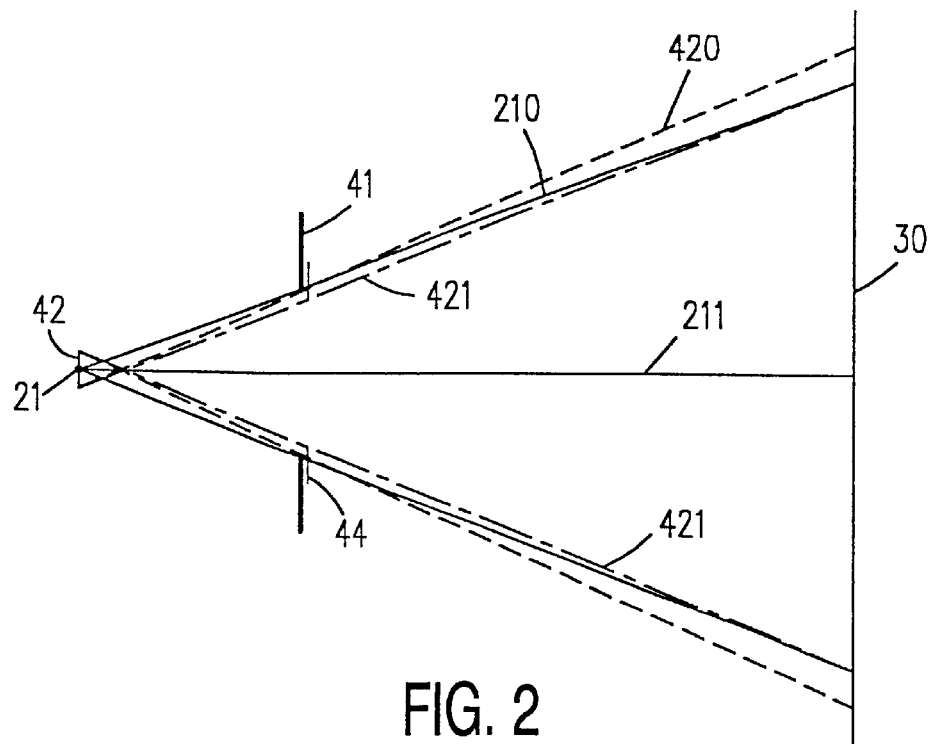
FIG. 2 shows the light cone and the radiation cone in such an X-ray examination apparatus.

The effect of the correction shutters will be described in detail hereinafter with reference to FIG. 2, wherein the central ray 211 does not extend vertically (as in FIG. 1) but horizontally. The filament 42 is taken to be particularly large in order to achieve a better illustration of the effects. Moreover, for the sake of simplicity of the drawing it is assumed that the light source 42 is situated at the location of the focal spot 21; because the optical distance between the filament 42 and the film, however, is exactly equal to the distance between the focal spot and the film, this assumption does not disturb the actual circumstances.

The radiation cone 210 emanating from the focal spot 21 is denoted by solid lines. Dashed lines represent the light cone 420 which would occur if the correction shutters 44 were absent. It is clearly shown that the illuminated field in the plane of the film 30, present in the moving grid, is substantially larger than the irradiated field. The correction shutters 44 constrict the light cone in such a manner that the light cone 421 (denoted by dash-dot lines) is obtained. When the width of the correction shutters is suitably chosen (the term "width" is to be understood to mean herein the distance between the light-limiting edge of the correction shutter 44 and the edge of the shutter plate 41 which limits the X-rays), the illuminated field can be made to correspond to the irradiated field.

The following equation suitably approximates the width b of the correction shutter:

$$b = \frac{1}{2}(B_s - B_x)\left(1 - \frac{d}{D}\right) \tag{1}$$

Therein, $B_s$ is the width of the light source, $B_x$ is the width of the focal spot, d is the distance between the plane of the shutter edges and the focal spot, and D is the distance between the focal spot and the film 30 (film-focus distance).

Using the practical values d=0.25 m, $B_s$=5 mm and $B_x$=1 mm, a value of 1.5 mm is then obtained for the width of the correction shutter in the case of a film-focus distance D of 1 m, and a value of 1.75 mm for a distance D amounting to 2 m. When the correction shutter 44 is rigidly connected to the shutter plate 41, the shutter width B is constant. In the case of a value B=1.5 mm, the image defects are completely corrected in the case of D=1 m (it would amount to 12 mm in the absence of correction shutters). In the case of a film-focus distance D of 2 m, the image defect is reduced from 28 mm to 3.5 mm. In this example the smallest exposure format that can still be adjusted amounts to 12 mm in the case of a film-focus distance D of 1 m. This value fully suffices in practice and amply meets the legally allowed maximum deviation of 20 mm between illuminated field and radiation field in the case of a film-focus distance D of 1 m.

The width of the correction shutter can also be proportioned for a value D of between 1 m and 2 m. The maximum image defect would then be smaller than in the assumed case. Generally speaking, however, the aim is for exact beam limiting at the standard distance (1 m, and recently also 1.15 m).

Figure 3:
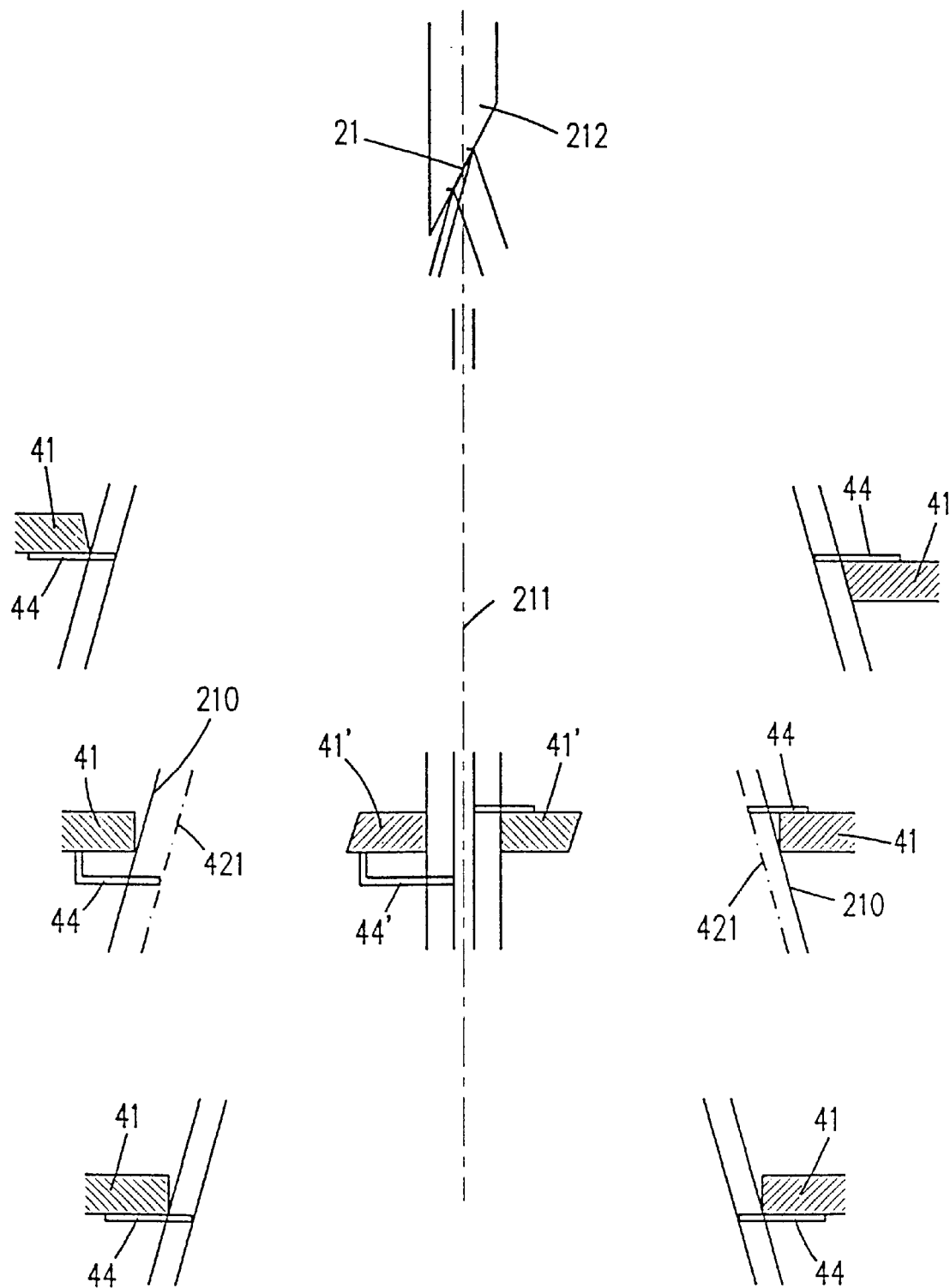
FIG. 3 shows various arrangements of the correction shutters on the shutter plates.

FIG. 3 shows diagrammatically various possibilities for arranging the correction shutters. Therein, the reference 212 denotes the anode disc of a rotary anode X-ray tube in which the focal spot 21 is situated on a focal spot track which is concentric with the horizontal axis of rotation of the anode disc 212. The focal spot track is inclined from 10° to 20° relative to the vertical, and the dimensions of the focal spot 21 are larger, in conformity with the principle of the strip focus, in the direction perpendicular to the focal spot track than in the direction of the focal spot track, so that the focal spot has a square appearance when viewed from the central ray 211. Because the plane of the focal spot track is inclined from the bottom left to the top right, the focal spot appears to be larger when viewed from the right-hand shutter edge than when viewed from the left-hand shutter edge. This means that the width $B_x$ of the focal spot appears to be larger at the right-hand side of the irradiated field than at the left-hand side thereof.

The various possibilities for arranging the correction shutters 44 are shown on three different rows in FIG. 3.

According to the lower row, the correction shutters are always situated underneath the shutter plates 41 and have the same width. This arrangement requires the least manufacturing and assembly work, but has the drawback that the diaphragm cannot be closed so far that it is no longer traversed by any X-rays; this is because the shutters cannot be closed further as soon as the facing shutter edges of the correction shutters 44 contact one another. It is to be noted, however, that complete closure of the shutter plates will not be required in practice. However, in given circumstances the correction shutters 44 could be resiliently connected to the shutter plates 41 so that the correction shutters would be displaced against the spring force upon closure.

The upper row of FIG. 3 shows a different arrangement of the correction shutters 44. One correction shutter 44 is now connected to the lower side of the left-hand shutter plate 41 and the other correction shutter is rigidly connected to the upper side of the right-hand shutter plate 41. In this case the complete closure of the shutter plates for the X-rays is not impeded by the correction shutters.

The second row shows an arrangement which is similar to that shown on the upper row, one of the two correction shutters (the lower left shutter in the present example) being situated at a given distance from the associated shutter plate. The edge ray of the radiation cone 210 (solid line) and of the light cone 421 (dashed line) is shown for the left-hand side as well as for the right-hand side.

It appears that for the right-hand shutter plate these edge rays are situated nearer to one another in comparison with those for the left-hand shutter plate. Consequently, the correction of the light cone by the correction shutter 44 at the right-hand side is less than that at the left-hand side, as required in conformity with the equation 1, because the focal spot appears to be larger when viewed from the side of the right-hand shutter than from the side of the left-hand shutter. The asymmetry caused by the asymmetrical position of the focal spot track relative to the two shutter edges is thus compensated for. However, when the shutter plates are closed, i.e. the shutter plates and the correction shutters occupy the positions denoted by the references 41' and 44', respectively, the asymmetry is reduced so that the edge rays of the light cone and of the radiation cone are symmetrically situated relative to the central ray 211.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An X-ray examination apparatus comprising:

an X-ray source and a diaphragm unit connected to the X-ray source, the diaphragm unit further comprising shutters for limiting a radiation cone beam emanating from a focal spot of the X-ray source, and a light source for generating a light cone beam which traverses the shutters via a reflector device, wherein the shutters include correction shutters which are transparent to X-rays but impervious to light and limit the light cone beam and two preferably adjustable pairs of shutter plates having pair-wise parallel shutter edges for limiting the radiation cone beam in two mutually perpendicular directions, wherein one of the correction shutters is connected to each shutter plate in such a manner that its edge extends parallel to the shutter edge and wherein the correction shutters connected to a pair of shutter plates are situated in mutually offset planes.

2. An X-ray examination apparatus comprising:

an X-ray source and a diaphragm unit connected to the X-ray source, the diaphragm unit further comprising shutters for limiting a radiation cone beam emanating from a focal spot of the X-ray source, and a light source for generating a light cone beam which traverses the shutters via a reflector device, wherein the shutters include correction shutters which are transparent to X-rays but impervious to light and limit the light cone beam and two preferably adjustable pairs of shutter plates having pair-wise parallel shutter edges for limiting the radiation cone beam in two mutually perpendicular directions, wherein one of the correction shutters is connected to each shutter plate in such a manner that its edge extends parallel to the shutter edge, wherein the correction shutters connected to a pair of shutter plates are situated in mutually offset planes, wherein the focal spot of the X-ray source is inclined relative to the planes of the correction shutters, and wherein the offset between the planes of the correction shutters is chosen to be such that the asymmetry of the radiation cone beam, imposed by the inclination, is at least partly compensated for by a corresponding asymmetry of the light cone beam.

\* \* \* \* \*